US012667598B2

(12) United States Patent
Kang et al.

(10) Patent No.: US 12,667,598 B2
(45) Date of Patent: Jun. 30, 2026

(54) *LACTOBACILLUS PARACASEI* ATG-EI STRAIN OR COMPOSITION COMPRISING SAME FOR PREVENTING OR TREATING RESPIRATORY DISEASE

(71) Applicants: ATOGEN CO., LTD, Daejeon (KR); Ji Hee Kang, Daejeon (KR)

(72) Inventors: Ji Hee Kang, Daejeon (KR); Young Sil Lee, Sejong (KR); Dae Young Lee, Daejeon (KR); Sung Hoon Im, Sejong (KR); Il Yong Ji, Daejeon (KR); Gun Seok Park, Daejeon (KR); Seung Hyun Ko, Sejong-si (KR); Juy I Park, Daejeon (KR); You Kyung Lee, Daejeon (KR)

(73) Assignees: ATOGEN CO., LTD, Daejeon (KR); Ji Hee Kang, Daejeon (KR)

( * ) Notice: Subject to any disclaimer, the term of this patent is extended or adjusted under 35 U.S.C. 154(b) by 223 days.

(21) Appl. No.: 18/580,997

(22) PCT Filed: Jun. 14, 2022

(86) PCT No.: PCT/KR2022/008333
§ 371 (c)(1),
(2) Date: Jan. 19, 2024

(87) PCT Pub. No.: WO2023/003175
PCT Pub. Date: Jan. 26, 2023

(65) Prior Publication Data
US 2025/0090605 A1 Mar. 20, 2025

(30) Foreign Application Priority Data
Jul. 23, 2021 (KR) ........................ 10-2021-0097130

(51) Int. Cl.
| | |
|---|---|
| *A61K 35/747* | (2015.01) |
| *A61K 9/00* | (2006.01) |
| *A61K 9/20* | (2006.01) |
| *A61P 11/00* | (2006.01) |
| *A61P 31/06* | (2006.01) |
| *C12N 1/205* | (2026.01) |
| *C12R 1/225* | (2006.01) |

(52) U.S. Cl.
CPC .......... *A61K 35/747* (2013.01); *A61K 9/0095* (2013.01); *A61K 9/2018* (2013.01); *A61K 9/2059* (2013.01); *A61K 9/2063* (2013.01); *A61P 11/00* (2018.01); *A61P 31/06* (2018.01); *C12N 1/205* (2021.05); *C12R 2001/225* (2021.05)

(58) Field of Classification Search
None
See application file for complete search history.

(56) References Cited

U.S. PATENT DOCUMENTS

2020/0054698 A1 2/2020 Lal et al.

FOREIGN PATENT DOCUMENTS

| | | |
|---|---|---|
| KR | 10-1500974 B1 | 3/2015 |
| KR | 10-1951919 B1 | 2/2019 |
| KR | 10-2049700 B1 | 11/2019 |
| KR | 10-2098067 B1 | 4/2020 |
| KR | 10-2163551 B1 | 10/2020 |
| KR | 10-2165930 B1 | 10/2020 |
| KR | 10-2020-0140225 A | 12/2020 |

OTHER PUBLICATIONS

J. Wassenberg et al., "Effect of Lactobacillus paracasei ST11 on a nasal provocation test with grass pollen in allergic rhinitis", Clinical & Experimental Allergy, 2011, vol. 41, pp. 565-573 (9 pages total).
Extended European Search Report dated Feb. 20, 2025 from the European Patent Office in Application No. 22846047.3.
Ching-Hung Lin et al., "Administration of Lactobacillus paracasei HB89 mitigates $PM_{2.5}$-induced enhancement of inflammation and allergic airway response in murine asthma model", PLOS ONE, Dec. 7, 2020, pp. 1-12, vol. 15, No. 12.
Xifan Wang et al., Oral administration of Lactobacillus paracasei L9 attenuates $PM_{2.5}$-induced enhancement of airway hyperresponsiveness and allergic airway response in murine model of asthma, PLOS ONE, Feb. 15, 2017, pp. 1-18, vol. 12, No. 2.
International Search Report for PCT/KR2022/008333 dated Sep. 13, 2022.

*Primary Examiner* — Brian Gangle
(74) *Attorney, Agent, or Firm* — Sughrue Mion, PLLC

(57) ABSTRACT

A novel strain, *Lactobacillus paracasei* ATG-E1 (Accession No. KCTC 14245BP), and a composition containing the same for preventing or treating respiratory diseases which are caused by fine particulate matter. The *Lactobacillus paracasei* ATG-E1 strain reduces the number of immune cells bronchoalveolar and lung tissues and inhibits the expression of inflammatory cytokines such as interleukin-17A (IL-17A), tumor necrosis factor-α (TNF-α), macrophage inflammatory protein 2 (MIP2), C-X-C motif chemokine ligand 1 (CXCL-1), macrophage inflammatory protein-α (MIP-1α) or interleukin-6 (IL-6). Therefore, the *Lactobacillus paracasei* ATG-E1 strain can be used for a treatment or health functional food for various respiratory diseases such as acute and chronic bronchitis, catarrhal bronchitis, bronchitis obliterans, inflammatory bronchitis, bronchial asthma, atopic asthma, non-atopic asthma, atopic IgE-mediated asthma, allergic asthma, non-allergic asthma, chronic bronchoconstriction, acute bronchoconstriction, chronic obstructive pulmonary disease, bronchial adenoma, pulmonary tuberculosis, emphysema, lung abscess, pulmonary fibrosis, lung cancer, airway cancer, bronchoalveolar cancer, and bronchial cancer.

4 Claims, 5 Drawing Sheets
Specification includes a Sequence Listing.

Fig. 2

**P(0.001 vs NC; *P(0.005 & ****P(0.001 vs CTL

□ : PM10D    ↖ : Infiltration of inflammation cells    ↘ : collagen deposition    ↖ : goblet cells

Fig. 5

_Lactobacillus paracasei_ ATG-E1 16s rRNA base sequence

AGTCGAACGAGTTCTCGTTGATGATCGGTGCTTGCACCGAGATTCAACATGGAACGAGTGGCGG
ACGGGTGAGTAACACGTGGGTAACCTGCCCCTTAAGTGGGGGATAACATTTGGAAACAGATGCTAA
TACCGCATAGATCCAAGAACCGCATGGTTCTTGGCTGAAAGATGGCGTAAGCTATCGCTTTTGGAT
GGACCCGCGGCGTATTAGAGTTGGTGAGGTAATGGCTCACCAAGGCGATGATACGTAGCCGAAC
TGAGAGGTTGATCGGCCACATTGGGACTGAGACACGGCCCAAACTCCTACGGGAGGCAGCAGTA
GGGAATCTTCCACAATGGACGCAAGTCTGATGGAGCAACGCCGCGTGAGTGAAGAAGGCTTTCG
GGTCGTAAAACTCTGTTGTTGGAGAAGAATGGTCGGCAAGTAACTGTTGTCGGCGTGACGGTATC
CAACCAGAAAGCCACGGCTAACTACGTGCCAGCAGCCGCGGTAATACGTAGGTGGCAAGCGTTA
TCCGGATTTATTGGGCGTAAAGCGAGCGCAGGCGGTTTTTTAAGTCTGATGTGAAAGCCCTCGGC
TTAACCGAGGAAGCGCATCGGAAACTGGGAAACTTGAGTGCAGAAGAGGACAGTGGAACTCCAT
GTGTAGCGGTGAAATGCGTAGATATATGGAAGAACACCAGTGGCGAAGGCGGCTGTCTGGTCTG
TAACTGACGCTGAGGCTCGAAAGCATGGGTAGCGAACAGGATTAGATACCCTGGTAGTCCATGCC
GTAAACGATGAATGCTAGGTGTTGGAGGGGTTTCCGCCCTTCAGTGCCGCAGCTAACGCATTAAGC
ATTCCGCCTGGGGAGTACGACCGCAAGGTTGAAACTCAAAGGAATTGACGGGGGCCCGCACAA
GCGGTGGAGCATGTGGTTTAATTCGAAGCAACGCGAAGAACCTTACCAGGTCTTGACATCTTTTG
ATCACCTGAGAGATCAGGTTTCCCCTTCGGGGGGCAAAATGACAGGTGGTGCATGGTTGTCGTCA
GCTCGTGTCGTGAGATGTTGGGTTAAGTCCCGCAACGAGCGCAACCCTTATGACTAGTTGCCAGC
ATTTAGTTGGGCACTCTAGTAAGACTGCCGGTGACAAACCGGAGGAAGGTGGGGATGACGTCAA
ATCATCATGCCCCTTATGACCTGGGCTACACACGTGCTACAATGGATGGTACAACGAGTTGCGAG
ACCGCGAGGTCAAGCTAATCTCTTAAAGCCATTCTCAGTTCGGACTGTAGGCTGCAACTCGCCTA
CACGAAGTCGGAATCGCTAGTAATCGCGGATCAGCACGCCGCGGTGAATACGTTCCCGGGCCTT
GTACACACCGCCCGTCACACCATGAGAGTTTGTAACACCCGAAGCCGGTGGCGTAACCCTTTTAG
GGAGCGAGCCGTCTAA

LACTOBACILLUS PARACASEI ATG-EI STRAIN OR COMPOSITION COMPRISING SAME FOR PREVENTING OR TREATING RESPIRATORY DISEASE

CROSS REFERENCE TO RELATED APPLICATIONS

This application is a National Stage of International Application No. PCT/KR2022/008333 filed Jun. 14, 2022, claiming priority based on Korean Patent Application No. 10-2021-0097130 filed Jul. 23, 2021, the entire disclosures of which are incorporated herein by reference.

INCORPORATION BY REFERENCE OF SEQUENCE LISTING

The content of the electronically submitted sequence listing, file name: Q295036_sequence listing as filed; size: 4,164 bytes; and date of creation: Jan. 15, 2024, filed herewith, is incorporated herein by reference in its entirety.

TECHNICAL FIELD

The present disclosure relates to a novel strain, *Lactobacillus paracasei* ATG-E1 (Accession No. KCTC 14245BP), or a composition containing the same for preventing or treating respiratory diseases.

BACKGROUND ART

Fine dust is particulate matter that is suspended in the air or drifts down to the ground. The fine dust is produced by the burning of fossil fuels such as coal and oil as well as by the combustion in industrial sites and the combustion of vehicle fuels.

The fine dust is categorized by the diameter of the particles, with PM10 referring to particles smaller than 10 μm and PM2.5 referring to particles smaller than 2.5 μm. The fine dust is known to be so fine that it is not filtered out through nasal hair or bronchial mucosa and can enter the alveoli or brain directly when inhaled. Once fine dust enters the body, the cells responsible for immunity are triggered to remove the particulate matter to defend the body, which can lead to an inflammatory response. This inflammatory response in the airways, lungs, cardiovascular system, and brain has been reported to increase the prevalence of asthma, respiratory and pulmonary diseases, and premature mortality. Unlike bacteria, temporary toxic materials, or other substances entering the airways to cause damage to the lungs or respiratory system, fine dust cannot be fought off by the human immune system and cannot be driven out by any means once the fine dust enters the body through the respiratory tract. Furthermore, since it is impossible to know exactly what problems will result from the damage, there is an urgent need for new therapeutics that can prevent, mitigate, treat, or ameliorate the damage to the airways and lungs induced by fine particulate matter, and that can treat respiratory diseases caused thereby.

Lactobacilli, a class of probiotics, live symbiotically in the human digestive system and break down fiber and complex proteins into important nutritional components. Lactobacilli are anaerobic bacteria that break down and use carbohydrates to make lactic acid and thrive in low-oxygen environments. Recently, the prevention and treatment effects of lactobacilli on various diseases have been confirmed, and attempts have been made to develop health functional foods and treatments using the lactobacilli.

While conducting various studies on ways to treat respiratory diseases using Lactobacilli, the inventors confirmed that the new strain of *Lactobacillus paracasei* ATG-E1 regulates respiratory immunity and suppresses inflammatory responses caused by the toxicity of fine dust, and thus completed the present disclosure.

DOCUMENTS OF RELATED ART

Patent Document

Korean Patent No. 10-2165930 (Title of Disclosure: Composition Comprising Lactic Acid Bacteria for Treating Respiratory Diseases or Inflammatory Diseases caused by Stimulation of Fine Dust, Applicant: GC Wellbeing Corporation, Date of Registration: Oct. 7, 2020)

Korean Patent No. 10-2049700 (Title of Disclosure: Composition Comprising *Lactobacillus Reuteri* ATG-F4 for Preventing or Treating Muscle diseases, Applicant: AtoGEN Corporation, Date of Registration: Nov. 21, 2019)

Korean Patent No. 10-2163551 (Title of Disclosure: Composition Comprising *Lactobacillus Plantarum* ATG-K2 or ATG-K6 for Preventing and Treating Lipid-related Metabolic Diseases, Applicant: AtoGEN Corporation, Data of Registration: Sep. 29, 2020)

Korean Patent No. 10-1500974 (Title of Disclosure: *Lactobacillus Plantarum* HAC01 strain with Anti-inflammatory and Metabolic Disease Treatment Effect and Uses Thereof, Applicant: AtoGEN Corporation, Data of Registration: Mar. 4, 2015)

Korean Patent No. 10-1951919 (Title of Disclosure: Novel *Lactobacillus Reuteri* ATG-F4 Strain with Function of Enhancing Dopamine Secretion and Composition Comprising Same for Preventing or Treating Mental Illness, Applicant: AtoGEN Corporation, Date of Registration: Feb. 19, 2019)

DISCLOSURE

Technical Problem

The objective of the present disclosure is to provide a novel strain, *Lactobacillus paracasei* ATG-E1 (Accession No. KCTC 14245BP), and a composition containing the same for preventing or treating respiratory diseases.

Technical Solution

The present disclosure relates to *Lactobacillus paracasei* ATG-E1 strain deposited under an accession number of KCTC 14245BP.

The strain may include a live cell, a dead cell, a culture, a culture fluid containing cells, a culture fluid from which cells have been removed, a concentrate of the culture, or a metabolite isolated from the cell or culture fluid.

The strain may have preventive or therapeutic efficacy for respiratory diseases induced by fine particulate matter.

The respiratory disease may be a disease selected from the group consisting of acute and chronic bronchitis, catarrhal bronchitis, bronchitis obliterans, inflammatory bronchitis, bronchial asthma, atopic asthma, non-atopic asthma, atopic IgE-mediated asthma, allergic asthma, non-allergic asthma, chronic bronchoconstriction, acute bronchoconstriction, chronic obstructive pulmonary disease, bronchial adenoma, pulmonary tuberculosis, emphysema, lung abscess, pulmonary fibrosis, lung cancer, airway cancer, bronchoalveolar cancer, and bronchial cancer.

The strain may have the effect of reducing the number of inflammatory cells and immunoregulatory cells in bronchoalveolar or lung tissue. Therefore, the *Lactobacillus paracasei* ATG-E1strain may have the effect of reducing the expression level of an inflammatory cytokine such as interleukin-17A (IL-17A), tumor necrosis factor-α (TNF-α), macrophage inflammatory protein 2 (MIP2), C-X-C motif chemokine ligand 1 (CXCL-1), macrophage inflammatory protein-α (MIP-1α) or interleukin-6 (IL-6).

The present disclosure relates to a pharmaceutical composition for treating or ameliorating respiratory diseases, the composition containing the *Lactobacillus paracasei* ATG-E1 strain.

The present disclosure provides a health functional food or food composition for preventing or ameliorating respiratory diseases, the health functional food or food composition containing the *Lactobacillus paracasei* ATG-E1 strain.

Hereinafter the present disclosure will be described in detail.

The *Lactobacillus paracasei* ATG-E1 strain is characterized in that it does not produce biogenic amines of histamine, tyramine, putrecine, and cadaverine.

The *Lactobacillus paracasei* ATG-E1 strain has acid resistance or bile resistance.

The *Lactobacillus paracasei* ATG-E1 strain has no resistance against one or more antibiotics selected from the group consisting of ampicillin, vancomycin, gentamicin, kanamycin, streptomycin, clindamycin, erythromycin, tetracycline, and chloramphenicol.

The composition containing the ATG-E1 strain of the present disclosure may contain one or more selected from the group consisting of a live cell of the strain, a killed cell of the strain, a culture of the strain, a culture fluid containing a cell of the strain, a culture fluid from which a cell of the strain has been removed, a concentrate of the culture fluid, and a metabolite isolated from the cell or culture.

The strain of the present disclosure can be cultured in a liquid (broth) or solid (agar) medium of MRS, to a concentration of about $1\times10^{10}$ CFU/mL.

The strain is preferably cultured at a temperature in the range of from 35° C. to 40° C. for 8 to 20 hours. The optimum temperature for cultivation is 37° C., the lowest temperature is 15° C., and the highest temperature is 45° C. In addition, the optimum pH for cultivation is 6.0, the minimum pH is 4.0, and the maximum pH is 7.8. The optimal cultivation time is 16 hours, with a minimum cultivation time of 8 hours and a maximum cultivation time of 24 hours.

The present disclosure also provides a pharmaceutical composition for the prevention or treatment of respiratory diseases, in which the pharmaceutical composition contains a novel strain, *Lactobacillus paracasei* ATG-E1. The novel *Lactobacillus paracasei* ATG-E1 strain may be contained in an amount of 0.001 to 100 wt % in the pharmaceutical composition of the present disclosure.

The pharmaceutical composition may be formulated and used in the form of oral formulations such as pills, granules, tablets, capsules, suspensions, emulsions, syrups, aerosols, and the like, or in the form of topical formulations, suppositories, and the like, in which the formulations are prepared according to conventional methods. Examples of carriers, excipients, and diluents that can be included in the pharmaceutical composition include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and mineral oil. When formulated, the formulations are prepared using commonly used diluents or excipients such as fillers, extenders, binders, wetting agents, disintegrants, and surfactants. Solid formulations for oral administration include tablets, pills, powders, granules, capsules, and the like. These solid formulations are prepared by adding at least one or more excipients such as starch, calcium carbonate, sucrose, lactose, gelatin, and the like to the composition. Aside from the simple excipients, lubricants such as magnesium stearate, talc, or the like may be additionally used. Liquid formulations for oral administration may include suspensions, solutions, emulsions, and syrups. Aside from a simple diluent such as water or liquid paraffin, the oral formulations may additionally contain various excipients such as wetting agents, sweetening agents, fragrances, preservatives, and the like. Formulations for parenteral administration include sterile aqueous solutions, non-aqueous solutions, suspensions, emulsions, lyophilized preparations, suppositories, and vaginal suppositories. For the non-aqueous solutions and suspensions, propylene glycol, polyethylene glycol, vegetable oils such as olive oil, injectable esters such as ethylolate, and the like may be used. As a base for suppositories, Witepsol, Macrogol, Wwin61, cacao butter, laurin butter, glycerogelatin, and the like may be used.

The dosage of the pharmaceutical composition of the present disclosure will depend on the age, sex, and weight of the subject to be treated, the specific disease or pathological condition to be treated, the severity of the disease or pathological condition, the route of administration, and the determination of the prescriber. Dosing decisions based on these factors may be made depending on the skill of those skilled in the art, and the doses may typically range from about 0.01 mg/kg/day to about 2000 mg/kg/day. More preferred doses range from 1 mg/kg/day to 500 mg/kg/day. The amount can be administered as a single once a day or may be administered as multiple doses. Such dosages should not be construed as limiting the scope of the present disclosure in any respect.

The pharmaceutical composition of the present disclosure can be administered to mammals, such as rats, livestock, and humans, by various routes. The strain of the present disclosure has little toxicity and side effects, so it is an agent that can be safely used for long-term use for prophylactic purposes.

In addition, the present disclosure also provides a health functional food pharmaceutical composition for the prevention or treatment of respiratory diseases, in which the health functional food contains a novel strain, *Lactobacillus paracasei* ATG-E1. The *Lactobacillus paracasei* ATG-E1 strain may be contained in an amount of 0.001 to 100 wt % in the health functional food of the present disclosure. The health functional food of the present disclosure is prepared in the form of pills, tablets, capsules, pills, or liquids. The health functional foods to which strain of the present disclosure can be added include, for example, various beverages, meats, sausages, breads, candies, snacks, noodles, ice creams, dairy products, soups, ionic beverages, sodas, alcoholic beverages, chewing gums, teas, and vitamin complexes.

Advantageous Effects

The present disclosure relates to a novel strain, *Lactobacillus paracasei* ATG-E1 (Accession No. KCTC 14245BP), and a composition containing the same for preventing or treating respiratory diseases which are caused by fine particulate matter. The *Lactobacillus paracasei* ATG-E1 strain inhibits the activity of inflammatory cells and various immune cells in bronchoalveolar and lung tissues and inhibits the expression of inflammatory cytokines such as interleukin-17A (IL-17A), tumor necrosis factor-α (TNF-α), macrophage inflammatory protein 2 (MIP2), C-X-C motif chemokine ligand 1 (CXCL-1), macrophage inflammatory protein-a (MIP2, MIP-1α) or interleukin-6 (IL-6). Therefore, the *Lactobacillus paracasei* ATG-E1 strain can be used for a treatment or health functional food for various respiratory diseases such as acute and chronic bronchitis, catarrhal bronchitis, bronchitis obliterans, inflammatory bronchitis, bronchial asthma, atopic asthma, non-atopic asthma, atopic IgE-mediated asthma, allergic asthma, non-allergic asthma, chronic bronchoconstriction, acute bronchoconstriction, chronic obstructive pulmonary disease, bronchial adenoma, pulmonary tuberculosis, emphysema, lung abscess, pulmonary fibrosis, lung cancer, airway cancer, bronchoalveolar cancer, and bronchial cancer.

DESCRIPTION OF DRAWINGS

FIG. 2 shows the results of determining the protein expression levels of intracellular inflammatory cytokines in bronchoalveolar lavage fluid derived from an animal model treated with the *Lactobacillus paracasei* ATG-E1 strain of the present disclosure and fine particulate matter.

FIG. 5 is a view showing the 16S rRNA base sequence of the *Lactobacillus paracasei* ATG-E1 of the present disclosure (SEQ ID NO: 1).

BEST MODE

Figure 1:
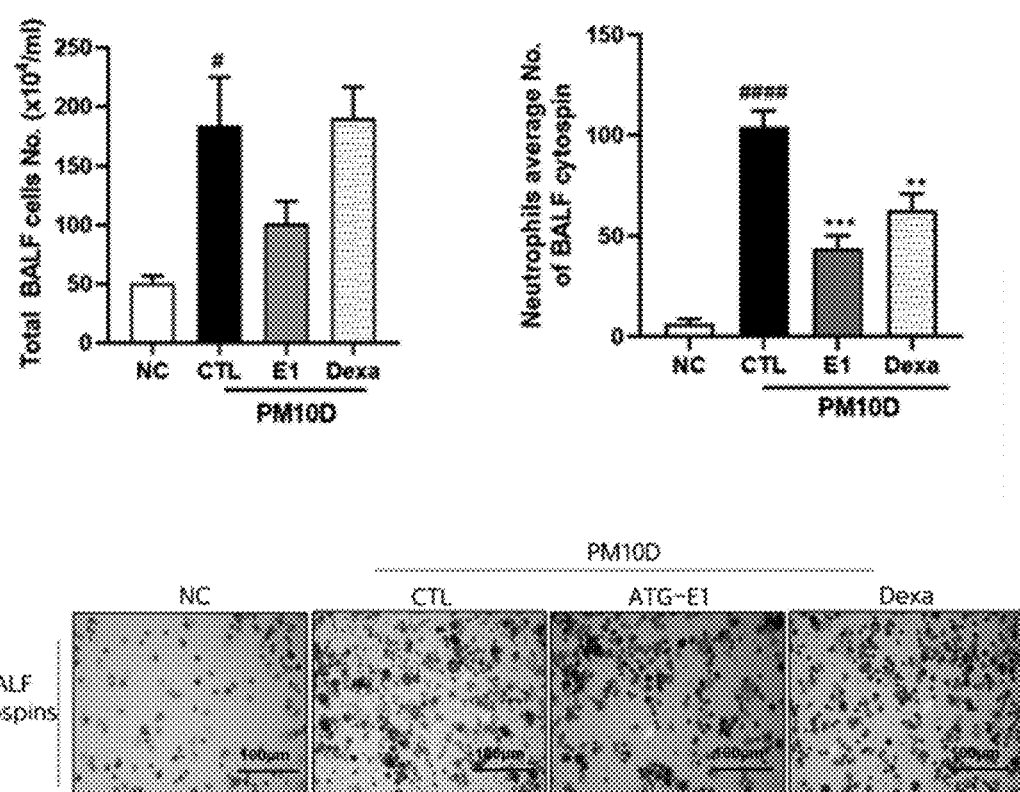
FIG. 1 shows the total cell count and neutrophils cell count in bronchoalveolar lavage fluid derived from an animal model treated with the *Lactobacillus paracasei* ATG-E1 strain of the present disclosure and fine particulate matter.

Hereinafter, preferred embodiments of the present disclosure will be described in detail. However, the present disclosure is not limited to the embodiments described herein and may be embodied in other forms. Rather, the embodiments are provided so that this disclosure will be thorough and complete and will fully convey the spirit of the disclosure to those skilled in the art.

Example 1. Isolation and Identification of a Novel Lactic Acid Bacterium, *Lactobacillus paracasei* ATG-E1

For strain isolation, baby (newborn) feces were obtained. 90 ml of physiological saline (0.85% NaCl/L) was added to an autoclaved bag, and 10 g of the raw sample (baby feces) was added thereto and mixed evenly. 1 ml of the sample mixture was dispensed, serially diluted 10-fold in 9 ml of physiological saline, and smeared on an MRS solid medium three times. Next, the strain was incubated in a 37° C. incubator for at least 48 hours, and the grown strain was analyzed by a catalase test using 0.3% hydrogen peroxide and Gram staining. The bacteria that were catalase-negative, Gram-positive, and *bacillus* rod-shaped were selected, and the 16S rDNA gene of the selected strain was sequenced. The sequence obtained by 16S rRNA sequencing was compared with the NCBI BLAST database. Since the 16S rRNA sequence of the strain was 99.9% identical to *Lactobacillus paracasei*, it was determined that the strain belonged to *Lactobacillus paracasei* in the taxonomic designation.

In addition, the completed whole genome sequence with a size of 3,124,497 bp was obtained using the MinION sequencing platform of Oxford Nanopore Technologies, and compared with the whole genome of the standard strain "*Lactobacillus paracasei* (ATCC 25302)" by the Average Nucleotide Identity (ANI) analysis. The analysis results showed 98.37% similarity, indicating a difference of 1.63% in the whole genome, meaning that the tested strain was a novel strain (Table 1). Therefore, the raw matter for the present application is named *Lactobacillus paracasei* ATG-E1, and the strain has been deposited at the Korean Collection for Type Cultures (KCTC) under the accession number "KCTC 14245BP".

TABLE 1

| Classification | Numerical value |
|---|---|
| ANI value | 98.37% |
| ATG-E1 genome size | 3,124,497 bp |
| Type strain genome size | 2,939,640 bp |

Example 2. Characterization of a Novel Lactic Acid Bacterium, *Lactobacillus paracasei* ATG-E1

Example 2-1. Sugar Utilization Characteristics

The sugar utilization characteristics of *Lactobacillus paracasei* ATG-E1 strain isolated according to the present disclosure were determined by using the API 50 CH test (Biomerieux) which was performed according to the instructions described in the manual. As a result, the *Lactobacillus paracasei* ATG-E1 strain of the present disclosure was observed to have the sugar utilization characteristics shown in Table 2 below.

TABLE 2

| Carbohydrate | Use for fermentation | Carbohydrate | Use for fermentation |
|---|---|---|---|
| Control | – | Esculin ferric citrate | + |
| Glycerol | – | Salicin | + |
| Erythritol | – | D-cellobiose | + |
| D-arabinose | – | D-maltose | + |
| L-arabinose | – | D-lactose | + |
| D-ribose | + | D-melibiose | – |
| D-xylose | – | D-saccharose (sucrose) | + |
| L-xylose | – | D-trehalose | + |
| D-adonitol | + | Inulin | – |
| Methyl-D-xylopyranoside | – | D-melezitose | + |
| D-lactose | + | D-raffinose | – |
| D-glucose | + | Amydon (starch) | + |
| D-fructose | + | Glycogen | – |
| D-manose | + | Xylitol | – |
| L-sorbose | + | Gentiobiose | + |

7

TABLE 2-continued

| Carbohydrate | Use for fermentation | Carbohydrate | Use for fermentation |
|---|---|---|---|
| L-rhamnose | – | D-turanose | + |
| Dulcitol | – | D-lyxose | – |
| Inositol | – | D-tagatose | + |
| D-manitol | + | D-fucose | |
| D-sorbitol | + | L-fucose | – |
| Methyl-D-xylopyranoside | – | D-arabitol | – |
| Methyl-D-xylopyranoside | + | L-arabitol | – |
| N-acetylglucosamine | + | Potassium Gluconate | + |
| Amygdalin | – | Potassium 2-KetoGluconate | + |
| Arbutin | + | Potassium 5-KetoGluconate | – |

Example 2-2. Test for Acid Resistance and Bile Resistance

Acid resistance and bile resistance tests of the strain were performed using the simulated stomach duodenum passage (SSDP) method under conditions similar to the human body (stomach and duodenum) environment. The isolated *Lactobacillus paracasei* ATG-E1 strain was cultured in MRS liquid medium for 18 hours, and then 1 ml of the strain fluid was collected in a tube and centrifuged (3000×g, 5 minutes, 4° C.). The supernatant was discarded, and the cell pellet was washed with physiological saline. The process was repeated twice. The saline was then removed, and the precipitated bacteria were mixed in 10 ml of MRS liquid

8

As confirmed from table 3, it can be seen that the survival rate of *Lactobacillus paracasei* ATG-E1 is very high under gastric acidic conditions while passing through bile to the small intestine.

Example 2-3 Antibiotic Resistance Test

The minimum inhibitory concentration (MIC) values of the antibiotics including ampicillin, vanacomycin, gentamicin, kanamycin, streptomycin, clindamycin, erythromycin, tetracycline, and chlorampenicol were determined using nine antibiotic E-test strips (BuoMerieux, France). Briefly, the lactic acid bacteria to be tested were suspended at an $OD_{600}$ absorbance of about 0.8 and smeared onto MRS solid media using a sterilized swab. The solid medium smeared with the lactic acid bacteria was dried for about 3 minutes, and an E-test strip was placed on the medium. The medium was incubated at 37° C. for about 48 hours. Due to the nature of lactic acid bacteria, intrinsic resistance against the aminoglycoside classes such as genetamicin, kanamycin, and streptomycin may be exhibited. Therefore, plate count agar (PCA, Difo Laboratories, USA) or Mueller-Hinton agar (MHA, Difco Laboratories, USA) was used as the test medium for these antibiotics. Guidelines published by the European Food Safety Authority (EFSA) were used to determine the types of antibiotics and the lowest inhibitory concentration that can be considered safe.

TABLE 4

| | AMP | VAN | GEN | KAN | STR | CD | ERY | TET | CM |
|---|---|---|---|---|---|---|---|---|---|
| *Lactobacillus paracasei* ATG-E1 | 2 | NR | 24 | 48 | 16 | 0.19 | 0.125 | 0.75 | 4 |
| European food safety authority (EFSA) | 4 | NR | 32 | 64 | 64 | 1 | 1 | 4 | 4 |

AMP: ampicillin; VAN: vancomycin, GEN: Gentamicin, KAN: kanamycin; STR: streptomycin; CD: clindamycin; ERY: erythromycin; TET: tetracyclin; CM: chloramphenicol; Cl: ciprofloxacin; NR: not required. (unit: μg/ml)

medium adjusted to pH 3. 1 ml of that suspension was taken, serially diluted 10-fold, smeared on MRS solid medium, and incubated for 24 to 48 hours at 37° C. After incubation at 37° C. for 24 to 48 hours, the number of bacteria produced was counted to determine the initial CFU/ml of the bacteria. The remaining 9 ml was incubated at 37° C. for 1 hour, and then successively mixed with bile acid and 17 ml of duodenal fluid. The bile acid was prepared by mixing 10 g of Ox gall with 100 ml of distilled water and autoclaving the mixture. The duodenal fluid was prepared by mixing duodenum juice, 6.4 g/L of $NaHCO_3$, 0.239 g/L of KCl, 1.28 g/L of NaCl in distilled water, adjusting the mixture to pH 7.4, and autoclaving the mixture. The survival rate of the bacteria was calculated by comparing the initial CFU/ml to the CFU/ml of the bacteria that survived after 3 hours.

TABLE 3

| | Early survival rate (%) | Survival rate (%) after one hour at pH 3.0 | Survival rate (%) after two or more hours in 3% Ox gall |
|---|---|---|---|
| *Lactobacillus paracasei* ATG-E1 | 100 | 73.0 | 51.48 |

The results of each assay are shown in Table 4. Table 4 shows the measurement results of the minimum inhibitory concentration (MIC) of *Lactobacillus paracasei* ATG-E1 (lactic acid bacteria) against major antibiotics. The strain of the present disclosure was found to exhibit a significantly lower level of antibiotic susceptibility than the limit suggested by the EFSA guidelines. This means that the strain "*Lactobacillus paracasei* ATG-E1" does not pose a risk of exchanging antibiotic resistance genes with other strains. In addition, when the pathogenicity of *Lactobacillus paracasei* ATG-E1 was predicted using PathogenFinder( ) along with the subsequent whole genome information, no cases were matched with pathogenic families and 480 cases were matched with non-pathogenic families, indicating that *Lactobacillus paracasei* ATG-E1 is a non-human pathogen and is not likely to be harmful to humans.

Example 2-4 Biogenic Amine Production Test

An MRS liquid medium added with 1% of amino acid precursors (L-tyrosine disodium salt, L-histidine monohydrochloride monohydrate, L-ornithine monohydrochloride, and L-lysine monohydrochloride) was prepared, and the isolated *Lactobacillus paracasei* ATG-E1 strain was inoculated on the MRS liquid medium containing the 1% amino acid precursors and subcultured for 5 to passages to activate decarboxylase. Enzyme-activated bacteria were smeared on a decarboxylase medium (tryptone 0.5%, yeast extract 0.5%, cocoon extract 0.5%, sodium chloride 0.5%, glucose 0.25%, Tween-80 0.05%, magnesium sulfate 0.02%, manganese sulfate 0.005%, iron sulfate 0.004%, citrate 0.2%, thiamine 0.001%, $K_2PO_4$ 0.2%, calcium carbonate 0.01%, pyridoxal-5-phosphate 0.005%, amino acid 1%, bromocresol purple 0.006%, and agar 2% were mixed in distilled water and adjusted to pH 5.3). The bacteria were then cultured at 37° C. for 48 hours to determine the ability to produce biogenic amines by checking whether the color changed to purple.

TABLE 5

|  | tyramine | histamine | putrescine | cadaverine |
|---|---|---|---|---|
| Lactobacillus paracasei ATG-E1 | — | — | — | — |

As shown in Table 5, as a result of analyzing whether ATG-EI strain can produce the biogenic amines including tyramine, histamine, putrescine, and cadaverine from the amino acid precursors including tyrosine, histidine, ornithine, and lysine, the results were confirmed to be negative. That is, the strain of the present disclosure does not have the ability to produce biogenic amines causing a hypersensitivity immune response.

Example 3. Prevention and Amelioration of Respiratory Damage Caused by Air Pollutants Such as Fine Dust

Example 3-1 Respiratory-Damaged Mouse Model Experiment

There were 8 Balb/c mice (male, 8 weeks old) per group, and all groups except a normal group were injected with a fine dust mixture using the Intra-Nazal-Trachea (INT) injection method described in literatures. The fine dust mixture contained diesel exhaust particles (DEP) (PM10 (Sigma)) and 1% (final concentration) of alum. The fine dust mixture was directly injected into the airways and noses of the experimental animals on days 4, 7, and 10 of the experiment. (Lim et al., Free Radic Biol Med. 25 (6), 635-644 (1998), Shin et al., Korean J. Mediclinal Crop Sci 27 (3), 218-231 (2019)). A positive control was administered orally daily for 10 days, dexamethasone (dexamethasone, also known as Dexa, Sigma, D2915) at a concentration of 3 mg/kg BW, and Lactic acid bacterium Lactobacillus paracasei ATG-E1 at a concentration of $4 \times 10^9$ CFU/mouse diluted in 0.5% sodium carboxymethyl cellulose solution (CMC, Sigma, 419273). An autopsy was performed on the 11th day after the start of the experiment, and bronchoalveloar lavage fluid (BALF) and lung tissue were collected.

Example 3-2 Measurement of Total Cell Count and Neutrophil Count in Bronchoalveolar Lavage Fluid (BALF)

On the last day of the experiment in Example 3-1, bronchoalveolar lavage fluid (BALF) was obtained after anesthesia, stained with 0.04% trypan blue, and the total number of cells was calculated using a hematocytometer to determine the total number of cells in the bronchoalveolar lavage fluid. Next, the sample was smeared with cytosine and stained with Diff-Qick, and the number of neutrophils was differentially calculated through optical microscopy.

As a result, the total number of cells and the number of neutrophils, which are inflammatory immune cells, in the bronchoalveolar lavage fluid were significantly increased in the fine dust-induced respiratory injury group (CTL), and the total number of cells in the bronchoalveolar lavage fluid tended to decrease in the group treated with Lactobacillus paracasei ATG-E1 (ATG-E1) after the respiratory injury was induced with the fine dust mixture. In addition, the number of neutrophils cells increased by the fine dust mixture (air pollutant) was significantly reduced, as shown in FIG. 1.

The results show that the administration of Lactobacillus paracasei ATG-E1 ameliorates the respiratory disease induced by the fine dust.

Example 3-3. Analysis of all Immune Cells in Bronchoalveolar Lavage Fluid (BALF)

Immune cell profiles (lymphocytes, neutrophils, macrophages, T cell subtypes, Gr-1$^+$CD11b$^+$, etc.) were measured by fluorescence-activated cell sorting (FACS) analysis of bronchoalveolar lavage fluid isolated from each individual after the end of the experiment in Example 3-1.

TABLE 6

| Cell phenotype | | NC | CTL | ATG-E1 | Dexa_3 mg/kg |
|---|---|---|---|---|---|
| | | | PM10D-induced airway inflammation model (Absolute No.) | | |
| Lymphocytes ($\times 10^7$ cells) | BAL | 0.08 ± 0.02 | 0.82 ± 0.05$^{####}$ | 0.87 ± 0.25 | 0.96 ± 0.53 |
| Neutrophils ($\times 10^7$ cells) | | 3.59 ± 0.73 | 15.09 ± 3.49$^{##}$ | 7.58 ± 1.40* | 15.01 ± 2.14 |
| Macrophage ($\times 10^7$ cells) | | 1.18 ± 0.14 | 1.82 ± 0.49 | 1.25 ± 0.15 | 2.29 ± 0.28 |
| CD4$^+$ ($\times 10^7$ cells) | | 0.07 ± 0.03 | 5.26 ± 1.14$^{####}$ | 2.18 ± 0.48** | 3.43 ± 0.58 |
| CD8$^+$ ($\times 10^7$ cells) | | 0.14 ± 0.08 | 3.72 ± 0.52$^{####}$ | 2.54 ± 0.52 | 2.80 ± 0.71 |
| CD4$^+$CD69$^+$ ($\times 10^7$ cells) | | 0.08 ± 0.04 | 1.73 ± 0.52$^{##}$ | 0.61 ± 0.10* | 1.40 ± 0.19 |
| CD62L$^-$CD44$^{+high}$ ($\times 10^7$ cells) | | 0.99 ± 0.21 | 6.40 ± 1.52$^{##}$ | 2.54 ± 0.41* | 5.95 ± 0.85 |
| Gr-1$^+$CD11b$^+$ ($\times 10^7$ cells) | | 0.34 ± 0.06 | 1.62 ± 0.42$^{##}$ | 0.79 ± 0.14 | 1.38 ± 0.12 |

$^{##}$P < 0.01 & $^{####}$P < 0.005 vs NC;
*P < 0.05 vs CTL

The number of each type of immune cells is shown in Table 6. In the CTL group in which the respiratory injury was induced with the fine dust mixture, the number of all immune cells was significantly increased. However, in the ATG-E1 group to which *Lactobacillus paracasei* ATG-E1 was administered after the respiratory injury was induced with the fine dust mixture, the number of neutrophils, CD4$^+$, and CD4$^+$CD69$^+$, which are immune cells, and the number of CD62L-CD44$^{+high}$ cells, which are specific markers for inflammatory response induced by the fine dust mixture, were significantly reduced.

Example 3-4. Analysis of Immune Cells in Cells Isolated from Lung Tissue

Immune cell profiles (lymphocytes, neutrophils, macrophages, T cell subtypes, Gr-1$^+$CD11b$^+$, etc.) were measured by fluorescence-activated cell sorting (FACS) analysis of bronchoalveolar lavage fluid isolated from lung tissue of each individual after the end of the experiment in Example 3-1.

TABLE 7

| Cell phenotype (FACS analysis) | | | PM10D-induced airway inflammation model (Absolute No.) | | |
|---|---|---|---|---|---|
| | | NC | CTL | ATG-E1 | Dexa_3 mg/kg |
| Lymphocytes ($\times 10^7$ cells) | Lung | 2.60 ± 0.64 | 3.17 ± 0.51 | 4.39 ± 0.83 | 9.34 ± 6.56 |
| Neutrophils ($\times 10^7$ cells) | | 3.03 ± 0.48 | 12.04 ± 2.26$^{\#\#}$ | 5.06 ± 0.67* | 3.41 ± 0.83** |
| Eosinophils ($\times 10^7$ cells) | | 1.56 ± 0.20 | 6.87 ± 0.97$^{\#\#\#}$ | 4.28 ± 1.02 | 3.41 ± 1.06 |
| CD4$^+$ ($\times 10^7$cells) | | 1.97 ± 0.35 | 6.13 ± 1.08$^{\#\#}$ | 3.39 ± 0.62* | 3.32 ± 0.42* |
| CD8$^+$ ($\times 10^7$ cells) | | 1.11 ± 0.23 | 3.46 ± 0.78$^{\#\#}$ | 1.84 ± 0.28 | 1.92 ± 0.18 |
| CD4$^+$CD69$^+$ ($\times 10^7$ cells) | | 0.20 ± 0.08 | 3.01 ± 1.08* | 0.46 ± 0.11* | 0.29 ± 0.07* |
| CD62L$^-$CD44$^{+high}$ ($\times 10^7$ cells) | | 0.35 ± 0.05 | 2.53 ± 0.50$^{\#\#}$ | 0.87 ± 0.06* | 1.27 ± 0.15 |
| CD21/35 + B220$^+$ ($\times 10^7$ cells) | | 0.27 ± 0.09 | 3.40 ± 0.72$^{\#\#\#}$ | 1.81 ± 0.35* | 1.35 ± 0.32** |
| Gr-1$^+$CD11b$^+$ ($\times 10^7$cells) | | 0.17 ± 0.05 | 1.07 ± 0.09$^{\#\#\#}$ | 0.38 ± 0.06*** | 0.60 ± 0.08*** |

$^{\#\#}$P < 0.01 & $^{\#\#\#}$P < 0.005 vs NC;
*P < 0.05 &
****P < 0.0005vs CTL

The results are shown in Table 7 below. The results showed that in the lung tissue, the number of all immune cells was significantly increased in the fine dust-induced respiratory injury group CTL, while the number of neutrophils, CD4+, CD4$^+$CD69$^+$, and CD62L-CD44$^{+high}$, CD21/35$^+$B220$^+$, and Gr-1$^+$CD11b$^+$ cells, which are specific markers for the fine dust-induced inflammatory response, were significantly reduced in the ATG-E1 group treated with *Lactobacillus paracasei* ATG-E1 after the respiratory injury was induced by the fine dust mixture.

Example 3-5. Measurement of Production of Total Inflammatory Factors in Bronchoalveolar Lavage Fluid (BALF)

The expression levels of inflammatory factors such as interleukin-17A (IL-17A), tumor necrosis factor-α (TNF-α), macrophage inflammatory protein 2 (MIP2), and C-X-C motif chemokine ligand 1 (CXCL-1) in the bronchoalveolar lavage fluid (BALF) of each of the individuals used in the experiment of Example 3-1 was measured with a commercially available ELISA kit (R&D system, USA) according to the test method provided by the manufacturer.

Figure 2:
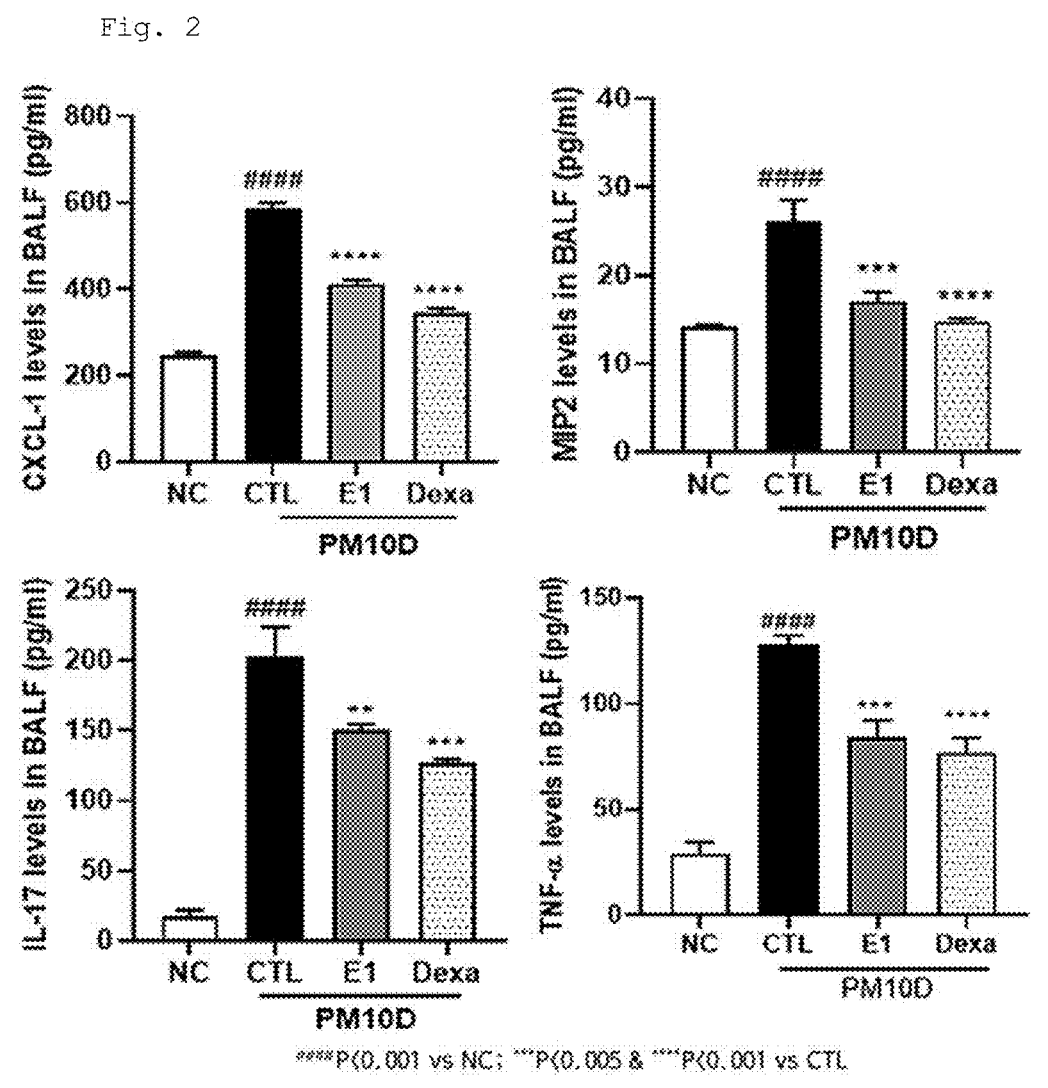

As shown in FIG. 2, the production levels of the inflammatory factors such as IL-17A, TNF-α, MIP2, and CXCL-1 were significantly increased in the CTL group with respiratory injury induced by the fine dust mixture, while the production levels of the inflammatory factors were significantly reduced in the ATG-E1 group because the mice in the group were treated with *Lactobacillus paracasei* ATG-E1 after suffering the respiratory injury induced by the fine dust mixture.

Example 3-6. Expression Analysis of Inflammatory Factors in Lung Tissue

Total RNA was extracted using RNAzol B reagent (Tel-Test, Austin, TX, USA) from the excised lung tissue of each of the individuals in the experiment of Example 3-1, and 3 μg of the total RNA was used to synthesize cDNA using ReverTraAce-a-cDNA Synthesis kit (Toyobo, Osaka, Japan). The synthesized DNA was subjected to real-time polymerase chain reaction (real-time PCR) using an Applied Biosystems 7500 Real-time PCR system (Applied Biosystems, USA) to analyze the expression levels of interleukin-6 (IL-6), TNF-α, CXCL-1, and MIP-1a. The real-time PCR was performed under such conditions that pre-denaturation was performed at 50° C. for 2 minutes, followed by heating at 94° C. for 10 minutes, followed by 40 cycles of treatment at 94° C. for 1 minute and 60° C. for 1 minute. The primer sequences used for genetic analysis are shown in Table 8. For the sample-administered group and the control group, the relative quantitative (RQ) was measured using GAPDH as an internal standard.

TABLE 8

| Gene | Sequence (5'-3') |
|---|---|
| IL-6 | Forward: TCCAGTTGCCTTCTTGGGAC (SEQ ID NO: 2) Reverse: GTGTAATTAAGCCTCCGACTTG (SEQ ID NO: 3) |
| TNF-α | Forward: GGCTTTCCGAATTCACTGGAGCCT (SEQ ID NO: 4) Reverse: CCCCGGCCTTCCAAATAAATACATTCATA SEQ ID NO: 5) |

TABLE 8-continued

| Gene | Sequence (5'-3') |
|------|------------------|
| MIP-1α | Forward: CACCATATGGCTCGGACACC (SEQ ID NO: 6) Reverse: TCAGGAAAATGACACCTGGCT (SEQ ID NO: 7) |
| CXCL1 | Forward: CCGAAGTCATAGCCACAC (SEQ ID NO: 8) Reverse: GTGCCATCAGAGCAGTCT (SEQ ID NO: 9) |
| GAPDH | Forward: GTCTTCCTGGGCAAGCAGTA (SEQ ID NO: 10) Reverse: CTGGACAGAAACCCCACTTC (SEQ ID NO: 11) |

Figure 3:
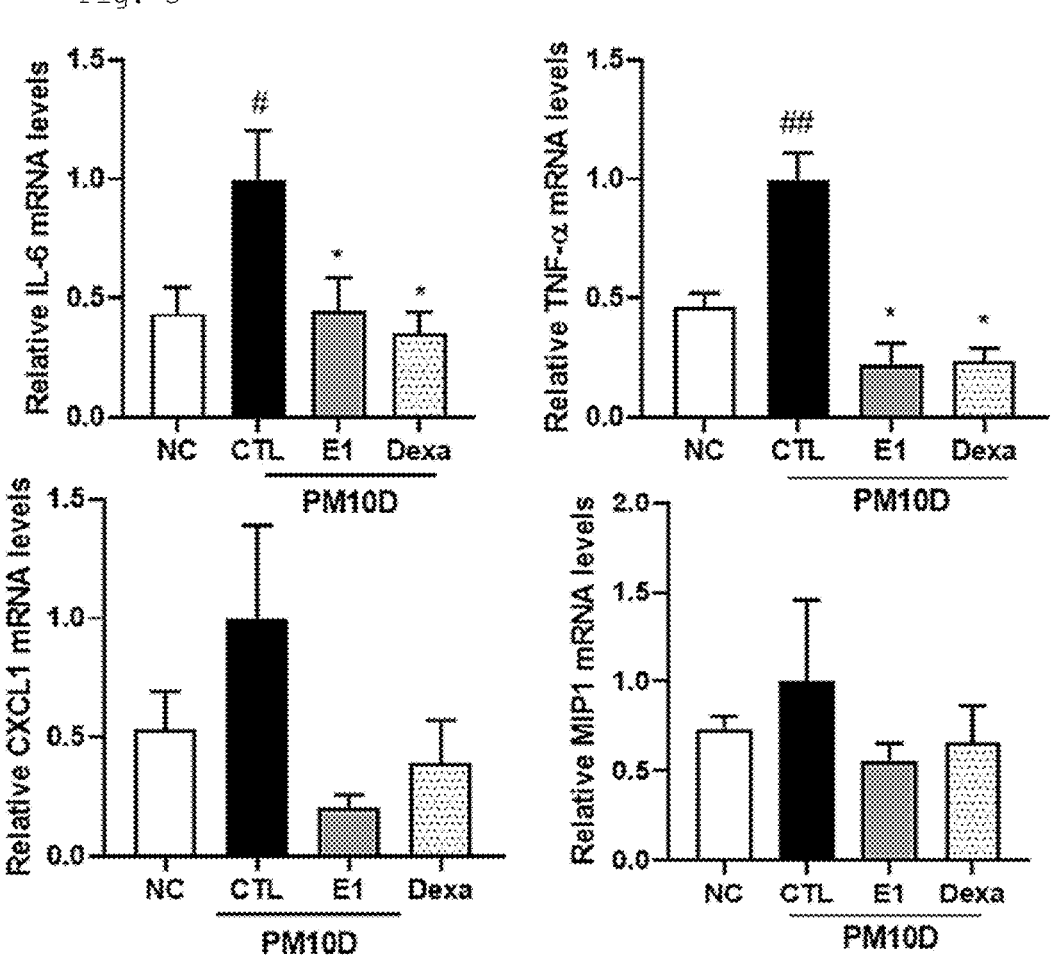
FIG. 3 shows the results of determining the mRNA expression levels of inflammatory cytokines in lung tissue cells of an animal model treated with the *Lactobacillus paracasei* ATG-E1 strain of the present disclosure and fine particulate matter.

The real-time PCR results are shown in FIG. 3. The results show that the expression of the inflammatory cytokines "IL-6, TNF-α, CXCL-1, and MIP-1α" was increased in the lung tissue of the fine dust-induced respiratory injury group CTL, but the gene expression of the inflammatory cytokines was significantly reduced by *Lactobacillus paracasei* ATG-E1 treatment.

Example 3-7. Histopathological Examination

The lung tissue was harvested from each of the individuals used in the experiment of Example 3-1, fixed in 10% neutral buffered formalin, and embedded in paraffin to prepare blocks from which tissue sections (4 μm thick) were prepared. Hematoxylin & Eosin (H&E) staining was then performed to observe inflammation in the lung tissue. Masson's trichrome (MT) staining for collagen deposition staining, and periodic acid Schiff (PAS) staining for mucus secretion staining were performed to observe pathological changes in the lung tissue through optical microscopy.

Figure 4:
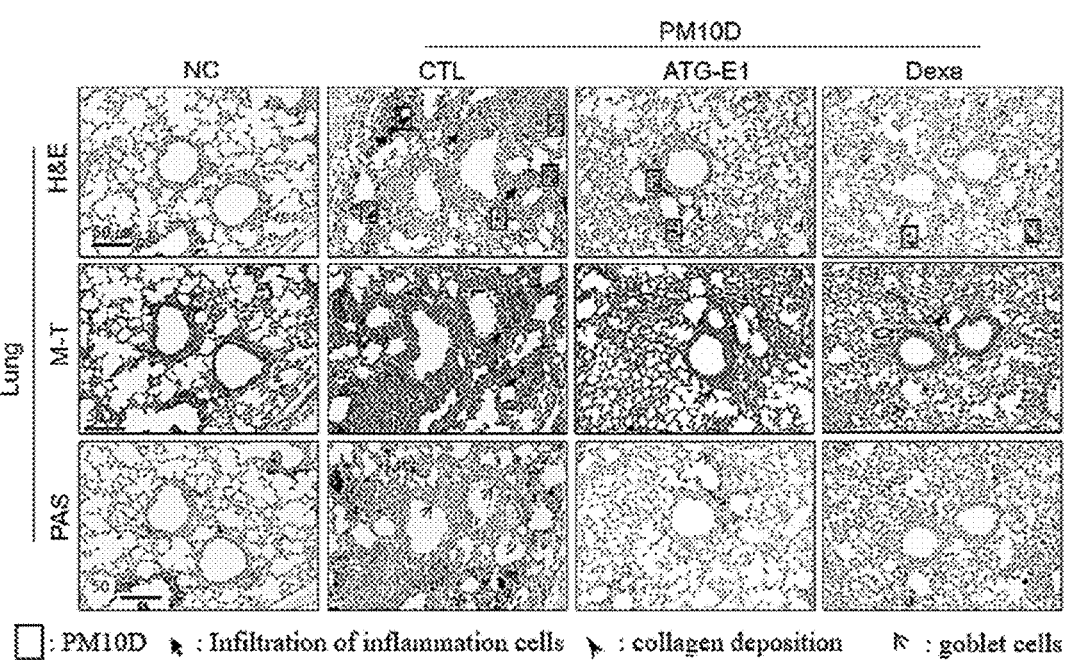
FIG. 4 shows photographs of stained lung tissue of an animal model treated with the *Lactobacillus paracasei* ATG-E1 strain of the present disclosure and fine particulate matter.
Figure 4:
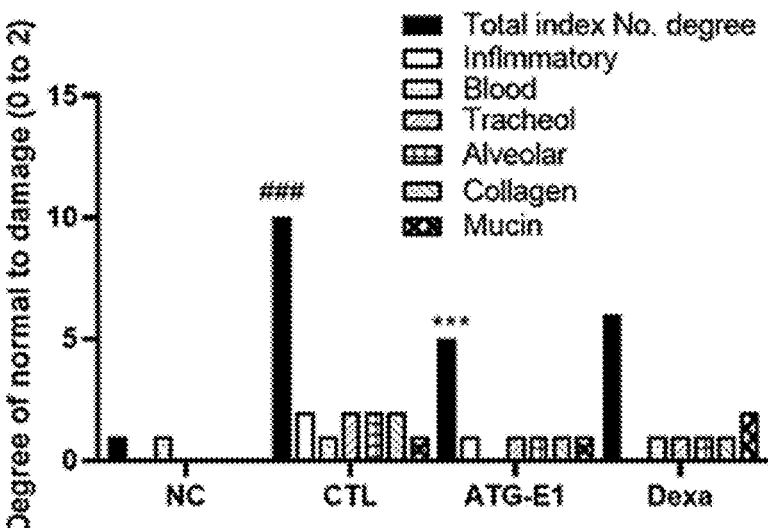

The observation results are shown in FIG. 4. The results show that the fine dust-induced respiratory injury group (CTL) had thickened lung cell walls, had increased collagen fibers, and exhibited inflammatory symptoms indicating tissue damage compared to the normal group, but the tissue damage was alleviated in the *Lactobacillus paracasei* ATG-E1 treatment group.

Formulation Example 1. Pharmacological Formulations

Formulation Example 1-1. <Preparation of Tablets>

200 g of *Lactobacillus paracasei* ATG-E1 of the present disclosure was mixed with 175.9 g of lactose, 180 g of potato starch, and 32 g of colloidal silicic acid. A 10% gelatin solution was added to the mixture, and the mixture was pulverized and passed through a 14-mesh sieve. The residue was dried and added with 160 g of potato starch, 50 g of talc, and 5 g of magnesium stearate, and the mixture was tableted.

Formulation Example 2. Preparation of Food

Formulation Example 2-1. Preparation of Cooking Seasonings

A health functional cooking seasoning was prepared by adding 1 wt % of *Lactobacillus paracasei* ATG-E1 of the present disclosure to a cooking seasoning.

Formulation Example 2-2. Preparation of Dairy Products

Various dairy products such as butter and ice cream were prepared by adding 0.1 wt % of *Lactobacillus paracasei* ATG-E1 of the present disclosure to milk.

Formulation Example 2-3. Preparation of Vegetable Juice

A health functional vegetable juice was prepared by adding 0.5 g of *Lactobacillus paracasei* ATG-E1 of the present disclosure to 1,000 ml of tomato juice or carrot juice.

Formulation Example 2-4. Preparation of Fruit Juice

A health functional fruit juice was prepared by adding 0.1 g of *Lactobacillus paracasei* ATG-E1 of the present disclosure to 1,000 ml of apple juice or grape juice.

Depository Authority

Name of Depository Authority: Korean Collection for Type Cultures, Korea Institute of Bioscience and Biotechnology Accession Number: KCTC 14245BP Date of Deposit: Jun. 21, 2020

The invention claimed is:

1. A method for treating a respiratory disease induced by fine particulate matter, comprising administering to a subject in need thereof *Lactobacillus paracasei* ATG-E1 strain having the accession number of KCTC 14245BP, wherein the respiratory disease is selected from the group consisting of bronchitis, asthma, emphysema and chronic obstructive pulmonary disease (COPD).

2. The method according to claim 1, wherein the strain comprises a live cell thereof or a killed cell thereof.

3. The method according to claim 1, wherein the subject requires reducing a number of inflammatory cells and immunoregulatory cells in a bronchoalveolar or lung tissue.

4. The method according to claim 1, wherein the subject requires reducing expression of inflammatory cytokines including interleukin-17A (IL-17A), tumor necrosis factor-$\alpha$ (TNF-$\alpha$), macrophage inflammatory protein 2 (MIP2), C-X-C motif chemokine ligand 1 (CXCL-1), macrophage inflammatory protein-1$\alpha$ (MIP-1$\alpha$) or interleukin-6 (IL-6).

\* \* \* \* \*

SEQUENCE LISTING

```
<160> NUMBER OF SEQ ID NOS: 11

<210> SEQ ID NO 1
<211> LENGTH: 1435
<212> TYPE: DNA
<213> ORGANISM: Lactobacillus paracasei

<400> SEQUENCE: 1
agtcgaacga gttctcgttg atgatcggtg cttgcaccga gattcaacat ggaacgagtg      60
gcggacgggt gagtaacacg tgggtaacct gcccttaagt gggggataac atttggaaac     120
agatgctaat accgcataga tccaagaacc gcatggttct tggctgaaag atggcgtaag     180
```

-continued

```
ctatcgcttt tggatggacc cgcggcgtat tagagttggt gaggtaatgg ctcaccaagg      240
cgatgatacg tagccgaact gagaggttga tcggccacat tgggactgag acacggccca      300
aactcctacg ggaggcagca gtagggaatc ttccacaatg gacgcaagtc tgatggagca      360
acgccgcgtg agtgaagaag gctttcgggt cgtaaaactc tgttgttgga gaagaatggt      420
cggcaagtaa ctgttgtcgg cgtgacggta tccaaccaga aagccacggc taactacgtg      480
ccagcagccg cggtaatacg taggtggcaa gcgttatccg gatttattgg gcgtaaagcg      540
agcgcaggcg gtttttttaag tctgatgtga aagccctcgg cttaaccgag gaagcgcatc      600
ggaaactggg aaacttgagt gcagaagagg acagtggaac tccatgtgta gcggtgaaat      660
gcgtagatat atggaagaac accagtggcg aaggcggctg tctggtctgt aactgacgct      720
gaggctcgaa agcatgggta gcgaacagga ttagataccc tggtagtcca tgccgtaaac      780
gatgaatgct aggtgttgga gggtttccgc ccttcagtgc cgcagctaac gcattaagca      840
ttccgcctgg ggagtacgac cgcaaggttg aaactcaaag gaattgacgg gggcccgcac      900
aagcggtgga gcatgtggtt taattcgaag caacgcgaag aaccttacca ggtcttgaca      960
tcttttgatc acctgagaga tcaggtttcc ccttcggggg caaaatgaca ggtggtgcat     1020
ggttgtcgtc agctcgtgtc gtgagatgtt gggttaagtc ccgcaacgag cgcaaccctt     1080
atgactagtt gccagcattt agttgggcac tctagtaaga ctgccggtga caaaccggag     1140
gaaggtgggg atgacgtcaa atcatcatgc cccttatgac ctgggctaca cacgtgctac     1200
aatggatggt acaacgagtt gcgagaccgc gaggtcaagc taatctctta aagccattct     1260
cagttcggac tgtaggctgc aactcgccta cacgaagtcg gaatcgctag taatcgcgga     1320
tcagcacgcc gcggtgaata cgttcccggg ccttgtacac accgcccgtc acaccatgag     1380
agtttgtaac acccgaagcc ggtggcgtaa ccctttttagg gagcgagccg tctaa         1435
```

```
<210> SEQ ID NO 2
<211> LENGTH: 20
<212> TYPE: DNA
<213> ORGANISM: Artificial Sequence
<220> FEATURE:
<223> OTHER INFORMATION: IL-6 Forward

<400> SEQUENCE: 2
tccagttgcc ttcttgggac                                                    20

<210> SEQ ID NO 3
<211> LENGTH: 22
<212> TYPE: DNA
<213> ORGANISM: Artificial Sequence
<220> FEATURE:
<223> OTHER INFORMATION: IL-6 Reverse

<400> SEQUENCE: 3
gtgtaattaa gcctccgact tg                                                 22

<210> SEQ ID NO 4
<211> LENGTH: 24
<212> TYPE: DNA
<213> ORGANISM: Artificial Sequence
<220> FEATURE:
<223> OTHER INFORMATION: TNF-alpha Forward

<400> SEQUENCE: 4
ggctttccga attcactgga gcct                                               24
```

<210> SEQ ID NO 5
<211> LENGTH: 29
<212> TYPE: DNA
<213> ORGANISM: Artificial Sequence
<220> FEATURE:
<223> OTHER INFORMATION: TNF-alpha Reverse

<400> SEQUENCE: 5
ccccggcctt ccaaataaat acattcata                                                    29

<210> SEQ ID NO 6
<211> LENGTH: 20
<212> TYPE: DNA
<213> ORGANISM: Artificial Sequence
<220> FEATURE:
<223> OTHER INFORMATION: MIP-1 alpha Forward

<400> SEQUENCE: 6
caccatatgg ctcggacacc                                                              20

<210> SEQ ID NO 7
<211> LENGTH: 21
<212> TYPE: DNA
<213> ORGANISM: Artificial Sequence
<220> FEATURE:
<223> OTHER INFORMATION: MIP-1 alpha Reverse

<400> SEQUENCE: 7
tcaggaaaat gacacctggc t                                                            21

<210> SEQ ID NO 8
<211> LENGTH: 18
<212> TYPE: DNA
<213> ORGANISM: Artificial Sequence
<220> FEATURE:
<223> OTHER INFORMATION: CXCL1 Forward

<400> SEQUENCE: 8
ccgaagtcat agccacac                                                                18

<210> SEQ ID NO 9
<211> LENGTH: 18
<212> TYPE: DNA
<213> ORGANISM: Artificial Sequence
<220> FEATURE:
<223> OTHER INFORMATION: CXCL1 Reverse

<400> SEQUENCE: 9
gtgccatcag agcagtct                                                                18

<210> SEQ ID NO 10
<211> LENGTH: 20
<212> TYPE: DNA
<213> ORGANISM: Artificial Sequence
<220> FEATURE:
<223> OTHER INFORMATION: GAPDH Forward

<400> SEQUENCE: 10
gtcttcctgg gcaagcagta                                                              20

<210> SEQ ID NO 11
<211> LENGTH: 20
<212> TYPE: DNA
<213> ORGANISM: Artificial Sequence
<220> FEATURE:
<223> OTHER INFORMATION: GAPDH Reverse -continued

```
<400> SEQUENCE: 11
ctggacagaa accccacttc                                                    20
```